US007309180B2

(12) United States Patent
Russell et al.

(10) Patent No.: US 7,309,180 B2
(45) Date of Patent: Dec. 18, 2007

(54) MULTIPURPOSE HYGIENIC IMPLEMENT

(76) Inventors: Syrenthia Russell, P.O. Box 16186, St. Petersburg, FL (US) 33733; Hunter Russell, 172 Russell William Rd., Eufaula, AL (US) 36027

( * ) Notice: Subject to any disclaimer, the term of this patent is extended or adjusted under 35 U.S.C. 154(b) by 244 days.

(21) Appl. No.: 11/077,761

(22) Filed: Mar. 11, 2005

(65) Prior Publication Data
US 2005/0201811 A1    Sep. 15, 2005

Related U.S. Application Data

(60) Provisional application No. 60/552,701, filed on Mar. 12, 2004.

(51) Int. Cl.
*A46B 11/08* (2006.01)

(52) U.S. Cl. .......................................... 401/1; 401/196

(58) Field of Classification Search ................ 401/1–3, 401/6, 185, 186, 188 R, 196, 202–207; 15/244.1, 15/244.2, 244.4
See application file for complete search history.

(56) References Cited

U.S. PATENT DOCUMENTS

| | | | | | |
|---|---|---|---|---|---|
| 4,961,661 | A | * | 10/1990 | Sutton et al. | 401/6 |
| 5,240,339 | A | * | 8/1993 | DeForest et al. | 401/207 |
| 5,360,111 | A | * | 11/1994 | Arispe | 206/361 |
| 5,851,077 | A | * | 12/1998 | Trejo | 401/6 |

* cited by examiner

*Primary Examiner*—Huyen Le

(57) ABSTRACT

A combination back scratcher, washer, lotion warmer and applicator includes an elongated, hollow ergonomically designed shaft having a handle at an upper end and any one of a plurality of interchangeable pivotal heads at the lower end. A heated lotion tube is received within the shaft. A reciprocal trigger operates an air pump to deliver heated lotion from the tube to one of the interchangeable heads.

11 Claims, 1 Drawing Sheet

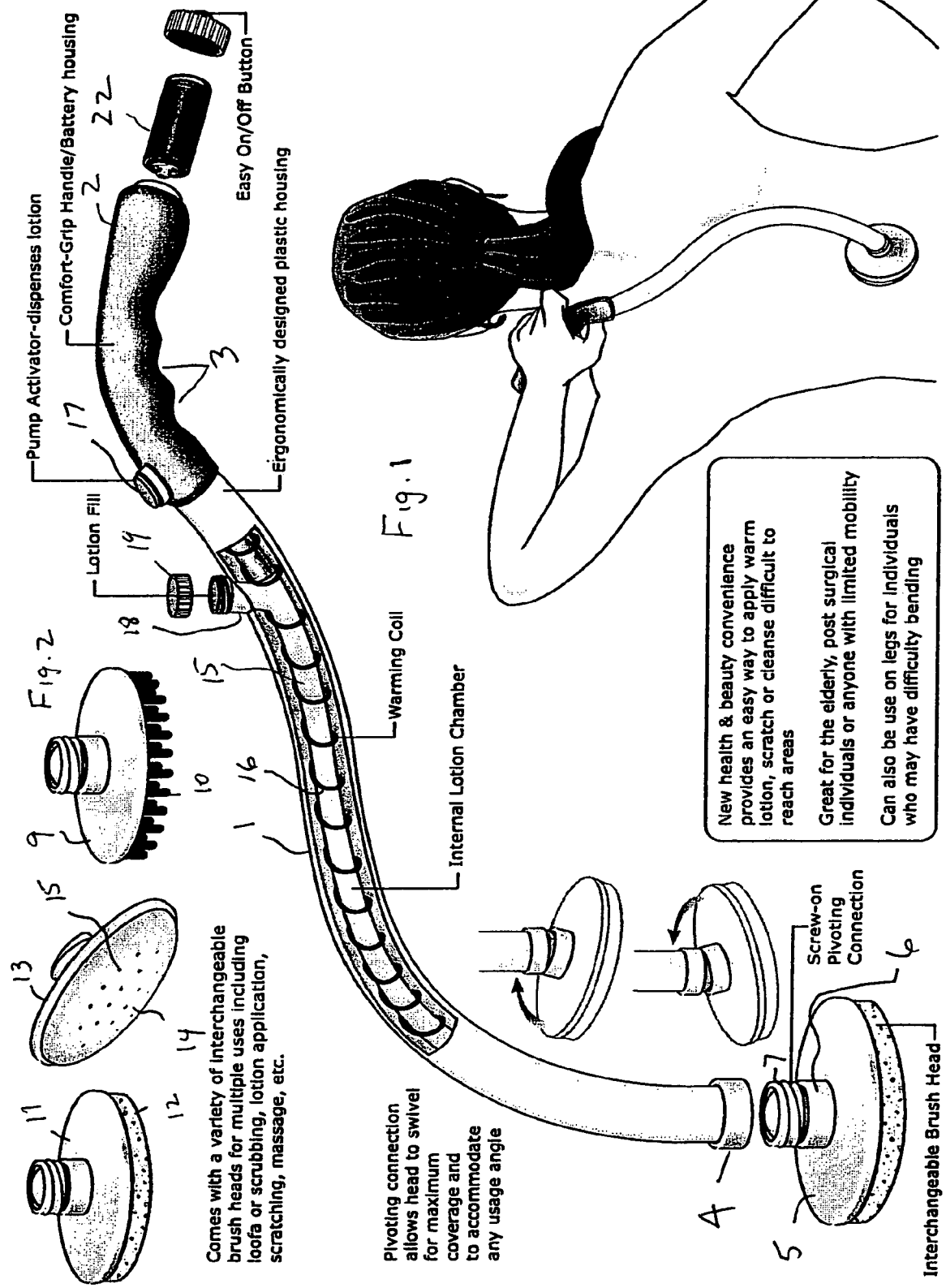

MULTIPURPOSE HYGIENIC IMPLEMENT

CROSS-REFERENCE TO RELATED APPLICATIONS

This application is a continuation application of provisional application No. 60/552,701 filed on Mar. 12, 2004.

BACKGROUND OF THE INVENTION

1. Field of Invention

The present invention relates to a multipurpose hygienic implement, specifically, a combination back washer, scratcher and lotion applicator.

2. Description of the Prior Art

The back is one of the most inaccessible areas of the body. However, one must often apply lotions, sun screen or soap to the back which may not be possible without the assistance of another person. Accordingly, there is currently a need for a device that allows an unassisted user to perform such tasks.

Although a myriad of lotion applicators and back scratchers exists in the prior art, none combine all of the features of the present invention, specifically, a lotion applicator, a lotion warmer, a back scratcher and a back washer. For example, U.S. Pat. No. D. 323,409 issued to Giese discloses an ornamental design for a lotion applicator including an acurate telescopic handle.

U.S. Pat. No. 6,0455279 issued to Follis discloses an easy reach applicator including an applicator head that uses a manually activated pressure plate regulator to maintain a positive pressure on the dispensing fluid.

U.S. Pat. No. 4,961,661 issued to Sutton, et al. discloses an extendable fluid applicator including a telescopic handle having a fibrous pad at an end thereof.

U.S. Pat. No. 5,834,410 issued to Slocum discloses a surface textured cleansing device including a plurality of cleaning teeth.

U.S. Pat. No. 5,573,342 issued to Patalano discloses a body lotion applicator system including a hollow tube for retaining lotion with an applicator pad attached thereto.

U.S. Pat. No. 37870,419 issued to Sage discloses a back scrubber/massager and lotion applicator including a body that receives soap with straps attached to each of two sides thereof. On one side of the body are a plurality of fingers while a plurality of projections extend from an opposing side.

As indicated above, although numerous applicators exist in the prior art, none include all of the features of the present invention, specifically, a lotion applicator including a plurality of interchangeable pivotal heads with an integral heated lotion storage tube.

SUMMARY OF THE INVENTION

The present invention relates to a hygienic implement including a lotion applicator, a lotion warmer, a back scratcher and a back washer. The device comprises an elongated, hollow, ergonomically designed shaft having an upper end and a lower end. On the upper end is a handle having finger indentions thereon. The lower end includes an internally threaded collar to which anyone of a plurality of brush heads may be removably attached. Each brush head includes a disc having an upper surface and a lower surface. On the upper surface of the disk is a band having an externally threaded nipple pivotally attached thereto for fastening to the collar. On the lower surface of each head is either a cleansing, dispensing or scratching surface. For example, a first brush head may include a plurality of bristles for scratching or massaging. A second head could have a sponge secured thereto for cleansing while a third could have a soft, bulbous surface with perforations thereon through which lotion or other solutions can be dispensed.

Received within the shaft and extending substantially the entire length thereof is a lotion storage tube. Helically wrapped about the lotion storage tube is a heating coil for heating the lotion to a desired temperature. An air pump delivers lotion from the storage tube to the cleaning head.

It is therefore an object of the present invention to provide a combination back washer, back scratcher, lotion warmer and lotion applicator.

It is another object of the present invention to provide an applicator and washing implement having a plurality of versatile interchangeable heads.

Other objects, features, and advantages of the present invention will become readily apparent from the following detailed description of the preferred embodiment when considered with the attached drawings and the appended claims.

BRIEF DESCRIPTION OF THE DRAWINGS

FIG. 1 is a perspective view of the cleaning implement.

FIG. 2 depicts the interchangeable cleaning heads.

DESCRIPTION OF THE PREFERRED EMBODIMENT

The present invention relates to a hygienic implement including a lotion applicator, a lotion warmer, a back scratcher and a back washer. The device comprises an elongated, hollow, ergonomically designed shaft 1 having an upper end and a lower end. On the upper end is a handle 2 having finger indentions 3 thereon. The lower end includes an internally threaded collar 4 to which anyone of a plurality of brush heads may be removably attached. Each brush head includes a disc 5 having an upper surface and a lower surface. On the upper surface of the disk is a band 6 having an externally threaded nipple 7 pivotally attached thereto for fastening to the collar. On the lower surface of each head is either a cleansing, dispensing or scratching surface. For example, a first brush head 9 may include a plurality of bristles 10 for scratching or massaging. A second head 11 could have a sponge 12 secured thereto for cleansing while a third 13 could have a soft, bulbous surface 14 with perforations 15 thereon through which lotion or other solutions can be dispensed.

Received within the shaft and extending substantially the entire length thereof is a lotion storage tube 15. A port 18 is disposed on the shaft for refilling the tube; the port is accessible with a removable cap 19. Helically wrapped about the lotion storage tube is a heating coil 16 for heating the lotion to a desired temperature. Within the handle is a compartment that receives batteries 22 for powering the coil. An air pump operable with a reciprocal trigger 17 delivers lotion from the storage tube to one of the interchangeable cleaning heads.

Specifically, the invention is a multipurpose hygienic implement used to wash, scratch, massage, warm or apply substances to a body surface. The invention has a handle, a head with a nipple pivotally attached and an elongated shaft. The elongated shaft is hollow with a storage tube therein and extends the length of the shaft. The shaft has an upper end releasably coupled with the handle. The elongated shaft has a lower end with a collar that releasable couples the nipple such that when the head is moved along a body surface the head swivels over the body surface for maximum coverage.

Further, the storage tube of the multipurpose hygienic implement has a means for heating contents within the storage tube. Specifically, the heating means is a coil that is wrapped around the storage for the full length or sectionally along the length of the storage tube.

The head of the multipurpose hygienic implement is comprised of a disk shaped member with an upper surface and a lower surface. The upper surface of the disk shaped member has a disk band with a nipple for coupling to the collar of the elongated shaft. The lower surface of the head may have attached thereto a sponge, a bulbous surface with perforations therein, or a plurality of bristles. The attachments may be interchangeable on the same head or a plurality of heads can be provided.

Additionally, the handle has an air pump therein that is activated by a reciprocal trigger along the handle. The air pump is coupled with the storage tube.

Lastly, the storage tube has a port that allows lotions, creams or other liquids to be placed inside the tube for subsequent release at the head through the activation of the air pump.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A multipurpose hygienic implement for use on the body comprising:
   a handle;
   a head;
   an elongated shaft being hollow with a storage tube therein and extending the length of the shaft, and the shaft having an upper end releasably coupled with the handle and a lower end releasable coupled with the head;
   the elongated shaft having a collar at the lower end; and
   the storage tube including a means for heating contents within the storage tube.

2. The multipurpose hygienic implement as set forth in claim 1, wherein the head is comprised of a disk shaped member with an upper surface and a lower surface, the upper surface having a disk band with nipple for coupling to the collar of the elongated shaft.

3. The multipurpose hygienic implement as set forth in claim 2, wherein the lower surface of the head may have attached thereto a sponge, a bulbous surface with perforations therein, or a plurality of bristles.

4. The multipurpose hygienic implement as set forth in claim 1, wherein the handle having an air pump therein that is activated by a reciprocal trigger along the handle; the air pump being coupled with the storage tube.

5. The multipurpose hygienic implement as set forth in claim 4, wherein the storage tube has a port to allow lotions, creams or other liquids to be placed inside the tube for subsequent release at the head through the activation of the air pump.

6. The multipurpose hygienic implement as set forth in claim 1, wherein the head when attached to the elongated shaft is use to wash, scratch, massage, warm or apply substances to a body surface.

7. A multipurpose hygienic implement used to wash, scratch, massage, warm or apply substances to a body surface comprising:
   a handle;
   a head with a nipple pivotally attached thereto;
   an elongated shaft being hollow with a storage tube therein and extending the length of the shaft, and the shaft having an upper end releasably coupled with the handle; and
   the elongated shaft having a lower end with a collar that releasable couples the nipple, wherein when the head is moved along a body surface the head swivels over the body surface for maximum coverage; and wherein the storage tube includes a means for heating contents within the storage tube.

8. The multipurpose hygienic implement as set forth in claim 7, wherein the head is comprised of a disk shaped member with an upper surface and a lower surface, the upper surface having a disk band with nipple for coupling to the collar of the elongated shaft.

9. The multipurpose hygienic implement as set forth in claim 8, wherein the lower surface of the head may have attached thereto a sponge, a bulbous surface with perforations therein, or a plurality of bristles.

10. The multipurpose hygienic implement as set forth in claim 1, wherein the handle having an air pump therein that is activated by a reciprocal trigger along the handle; the air pump being coupled with the storage tube.

11. The multipurpose hygienic implement as set forth in claim 1, wherein the storage tube has a port to allow lotions, creams or other liquids to be placed inside the tube for subsequent release at the head through the activation of the air pump.

* * * * *